US 11,034,679 B2

(12) United States Patent
Prisinzano et al.

(10) Patent No.: US 11,034,679 B2
(45) Date of Patent: Jun. 15, 2021

(54) AGONISTS OF THE MU OPIOID RECEPTOR

(71) Applicants: UNIVERSITY OF KANSAS, Lawrence, KS (US); VICTORIA LINK LIMITED, Wellington (NZ)

(72) Inventors: Thomas E. Prisinzano, Lawrence, KS (US); Rachel Saylor Crowley, San Diego, CA (US); Bronwyn Maree Daken Kivell, Wellington (NZ)

(73) Assignees: UNIVERSITY OF KANSAS, Lawrence, KS (US); VICTORIA LINK LIMITED, Wellington (NZ)

(*) Notice: Subject to any disclaimer, the term of this patent is extended or adjusted under 35 U.S.C. 154(b) by 0 days.

(21) Appl. No.: 16/763,163

(22) PCT Filed: Nov. 14, 2018

(86) PCT No.: PCT/US2018/061148
§ 371 (c)(1),
(2) Date: May 11, 2020

(87) PCT Pub. No.: WO2019/099588
PCT Pub. Date: May 23, 2019

(65) Prior Publication Data
US 2020/0385368 A1 Dec. 10, 2020

Related U.S. Application Data

(60) Provisional application No. 62/586,639, filed on Nov. 15, 2017.

(51) Int. Cl.
| *C07D 405/14* | (2006.01) |
| *C07D 407/12* | (2006.01) |
| *C07D 407/14* | (2006.01) |
| *A61P 25/00* | (2006.01) |
| *A61P 25/04* | (2006.01) |
| *A61P 29/00* | (2006.01) |
| *C07D 407/04* | (2006.01) |

(52) U.S. Cl.
CPC ............ *C07D 407/14* (2013.01); *A61P 29/00* (2018.01); *C07D 405/14* (2013.01); *C07D 407/04* (2013.01)

(58) Field of Classification Search
CPC ... C07D 405/14; C07D 407/12; C07D 407/14
See application file for complete search history.

(56) References Cited

U.S. PATENT DOCUMENTS

| 2009/0088466 A1 | 4/2009 | Bohn et al. |
| 2017/0313692 A1 | 11/2017 | Prisinzano et al. |

OTHER PUBLICATIONS

PCT Search Report and Written Opinion dated Mar. 13, 2019 for International Application No. PCT/US2018/061148.
Tidgewell et al., "Herkinorin Analogues with Differential Beta-Arrestin-2 Interactions", J. Med. Chem. 2008. vol. 51(8), pp. 2421-2431, entire document, especially: p. 21, Scheme 21, formula 3f.

*Primary Examiner* — Emily A Bernhardt
(74) *Attorney, Agent, or Firm* — Foley & Lardner LLP

(57) ABSTRACT

The present technology is directed to compounds, compositions, and methods related to non-morphinan-like mu opioid receptor agonists of Formula I. Compounds of the present technology demonstrate remarkable potency and selectivity for the mu opioid receptor, while also exhibiting a significant reduction (or, essentially, absence) of the negative side effects of many morphine-derived compounds.

16 Claims, 4 Drawing Sheets

AGONISTS OF THE MU OPIOID RECEPTOR

CROSS-REFERENCE TO RELATED APPLICATIONS

This application claims the benefit of and priority to U.S. Provisional Appl. No. 62/586,639, filed Nov. 15, 2017, the entirety of which is hereby incorporated by reference for any and all purposes.

U.S. GOVERNMENT RIGHTS

This application is a U.S. National Phase Application under 35 U.S.C. § 371 of International Application No. PCT/US2018/061148, filed Nov. 14, 2018, which claims the benefit of and priority to U.S. Provisional Appl. No. 62/586,639, filed Nov. 15, 2017, the entirety of each of which is hereby incorporated by reference for any and all purposes.

FIELD

The present technology is directed to compounds, compositions, and methods related to non-morphinan-like mu opioid receptor (MOR) agonists.

SUMMARY

In an aspect, a compound according to Formula I is provided

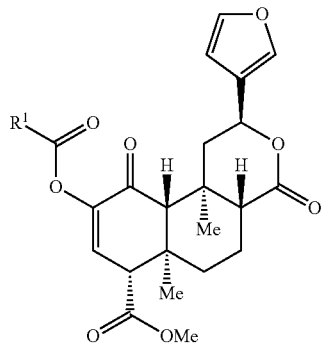

(I)

or a pharmaceutically acceptable salt and/or solvate thereof, wherein
$R^1$ is

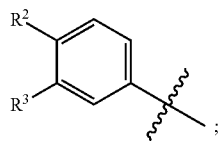

$R^2$ is a substituted $C_1$-$C_3$ alkyl, —C(O)H, —C(O)—$C_1$-$C_3$ alkyl, or —C(O)—$NR^4R^5$, and
$R^3$ is H, halo, substituted $C_1$-$C_3$ alkyl, or $C_1$-$C_3$ alkoxy; or
$R^2$ and $R^3$ combined are heterocyclyl or heteroaryl; and
$R^4$ and $R^5$ are each independently H or $C_1$-$C_3$ alkyl.

In a related aspect, a composition is provided that includes the compound and a pharmaceutically acceptable carrier.

In another related aspect, a pharmaceutical composition is provided, the pharmaceutical composition including an effective amount of the compound for treating pain.

DESCRIPTION OF THE DRAWINGS

FIG. 2A provides the time course of analgesic effects in the hot water tail-flick assay and FIG. 2B provides an area under the curve ("AUC") analysis, where $p<0.01$, *$p<0.001$, ****$p<0.0001$, drug compared to vehicle, #$p<0.05$, ##$p<0.01$, ###$p<0.001$, ####$p<0.0001$ compared to morphine, ^^^^$p<0.0001$ 3.46 compared to 3.46+β-FNA. Data shown as mean±SEM (N=5-7 per group).

DETAILED DESCRIPTION

Figure 1A:
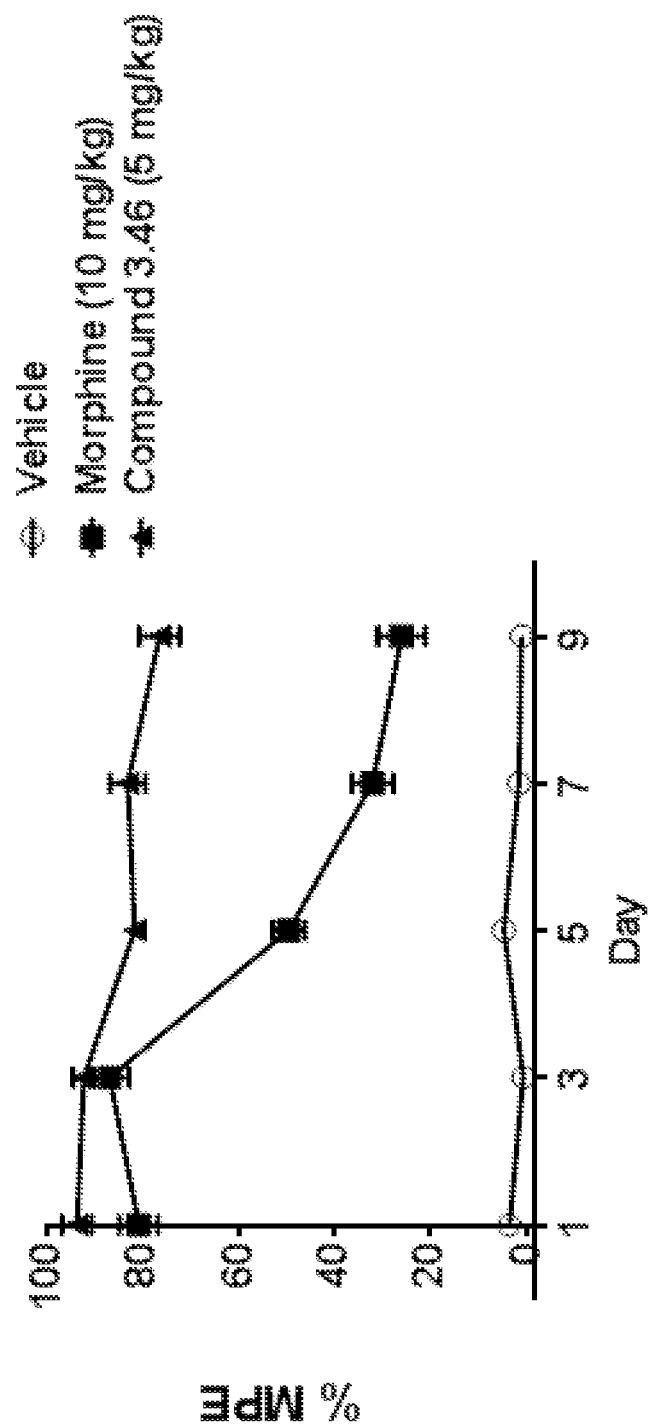
FIGS. 1A-B show the results of the hot water tail-flick assay in mice for a compound of the present technology (compound 3.46) as compared to morphine. For FIGS. 1A-B, data shown as mean±SEM.

In various aspects, the present technology provides compounds and methods for agonizing a mu opioid receptor. The compounds provided herein can be formulated into pharmaceutical compositions and medicaments that are useful in the disclosed methods. Also provided is the use of the compounds in preparing pharmaceutical formulations and medicaments.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 wt. %" would mean "9 wt. % to 11 wt. %."

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH($CH_3$), —CH=C($CH_3$)$_2$, —C($CH_3$)=$CH_2$, —C($CH_3$)=CH($CH_3$), —C($CH_2CH_3$)=$CH_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups may be substituted or unsubstituted. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡$CCH_3$, —$CH_2$C≡$CCH_3$, —C≡$CCH_2$CH($CH_2CH_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Aryl groups may be substituted or unsubstituted. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. The phrase "aryl groups" includes groups containing fused rings, such as fused aromatic-aliphatic ring systems (e.g., indanyl, tetrahydronaphthyl, and the like). Representative substituted aryl groups may be mono-substituted (e.g., tolyl) or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. Aralkyl groups may be substituted or unsubstituted. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. Heterocyclyl groups may be substituted or unsubstituted. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. The phrase includes heterocyclyl groups that have other groups, such as alkyl, oxo or halo groups, bonded to one of the ring members, referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be monosubstituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Alkoxy groups may be substituted or unsubstituted. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —COOR$^{70}$ and —C(O)O-G groups. R$^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while "sulfides" include —SR$^{80}$ groups, "sulfoxides" include —S(O)R$^{81}$ groups, "sulfones" include —SO$_2$R$^{82}$ groups, and "sulfonyls" include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O$^-$. A "hydroxyalkyl" group is a hydroxyl-substituted alkyl group, such as HO—CH$_2$—.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "isocyano" refers to —NC.

The term "isothiocyano" refers to —NCS.

The term "pentafluorosulfanyl" refers to —SF$_5$.

The phrase "selectively" or "selectivity" as used herein will be understood by persons of ordinary skill in the art and will vary to some extent depending upon the context in which the phrase is used. If there are uses of the phrase which are not clear to persons of ordinary skill in the art, given the context in which the phrase is used, the phrase at minimum refers to the compounds acting through a specific mechanism of action, resulting in fewer off-target effects because the compounds target a particular receptor over other receptors, such as a mu (μ) opioid receptor (MOR) over a kappa (κ) opioid receptor (KOR) and/or a delta (δ) opioid receptor (DOR). The phrase may further be modified as discussed herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

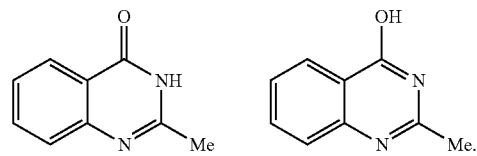 [SMILES: Cc1nc2ccccc2c(=O)[nH]1 ; Cc1nc(O)c2ccccc2n1]

As another example, guanidines may exhibit the following isomeric forms in protic organic solution, also referred to as tautomers of each other:

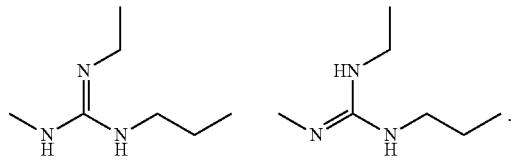

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

The Present Technology

Pain affects nearly 115 million Americans, which is more than cancer, heart disease, and diabetes combined. Unfortunately, the use of opioids, one of the most common drug classes used to treat pain, is problematic due to their high abuse liability. In 2014, an estimated 54 million people over the age of 12 had used prescription drugs, such as opioids, non-medically in their lifetimes. According to the Centers for Disease Control and Prevention (CDC), 2014 had the highest rate of drug overdose deaths than any year prior, with an estimated 40 Americans dying each day from overdosing on prescription painkillers. Thus, a strong analgesic devoid of abuse liabilities is desperately needed in an attempt to combat this trend and prevent these deaths.

The prototypical opioid, morphine, has been used for over a century for the management of pain, and its powerful analgesic effects have stimulated innumerable synthetic and semi-synthetic investigations aimed at optimizing its biological effects. While these studies have resulted in most of the clinically useful treatments for pain such as codeine, oxycodone, meperidine, methadone, and fentanyl, these drugs are not without drawbacks. All of these morphine-derived compounds are mu opioid receptor (MOR) agonists and suffer from adverse effects such as sedation, tolerance, dependence, constipation, and respiratory depression. Tolerance and dependence are particularly significant effects because they can lead to opioid addiction, which is often the most concerning effect for both patients and prescribers.

Most clinically used opioids are structurally similar to morphine and they all have very similar activity profiles. To date, it has been very difficult to differentiate opioid-induced analgesic activity from abuse liability.

The present technology provides opioids that demonstrate remarkable potency and selectivity for the MOR over the kappa opioid receptor (KOR) such as exhibiting $EC_{50}$ values for KOR>10,000 nM, while also exhibiting a significant reduction (or, essentially, absence) of the negative side effects of many morphine-derived compounds (such as tolerance, sedation, and/or liability for abuse).

Thus, in an aspect, a compound according to Formula I is provided

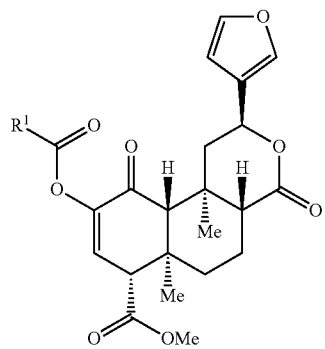
(I)

or a pharmaceutically acceptable salt and/or solvate thereof, wherein $R^1$ is

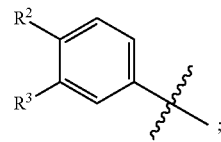

$R^2$ is a substituted $C_1$-$C_3$ alkyl, —C(O)H, —C(O)—$C_1$-$C_3$ alkyl, or —C(O)—$NR^4R^5$, and $R^3$ is H, halo, substituted $C_1$-$C_3$ alkyl, or $C_1$-$C_3$ alkoxy; or $R^2$ and $R^3$ combined are heterocyclyl or heteroaryl; and $R^4$ and $R^5$ are each independently H or $C_1$-$C_3$ alkyl.

In any embodiment herein, $R^2$ may be a hydroxyl-substituted $C_1$-$C_3$ alkyl, a $C_1$-$C_3$ alkoxy substituted $C_1$-$C_3$ alkyl, —C(O)—$C_1$-$C_3$ alkyl, or —C(O)—$NR^4R^5$. For example, in any embodiment $R^2$ may be hydroxymethyl, (R)-1-hydroxyethyl, (S)-1-hydroxyethyl, methoxymethyl, or —C(O)—$NH_2$. In any embodiment herein, it may be that $R^3$ is H or $R^2$ and $R^3$ combined are heterocyclyl or heteroaryl.

In any embodiment herein, it may be that when $R^2$ and $R^3$ combined are heterocyclyl or heteroaryl, $R^1$ is

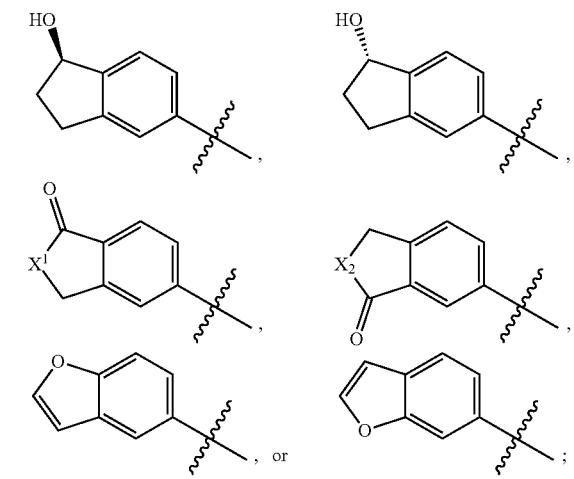

where $X^1$ and $X^2$ are each independently $CH_2$, O, or NH.

In any of the above embodiments, it may be that the compound is

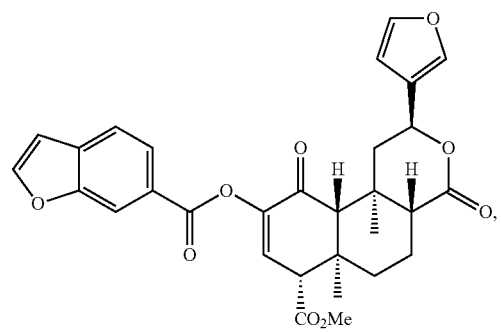

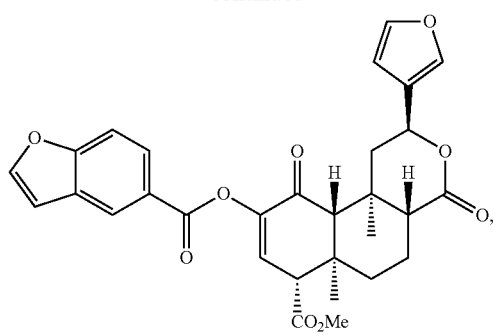
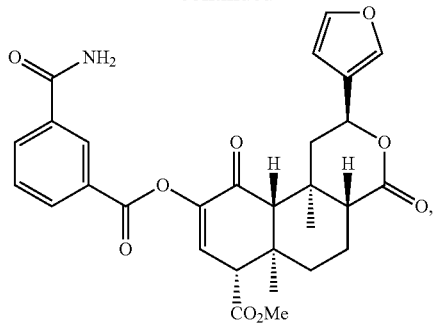
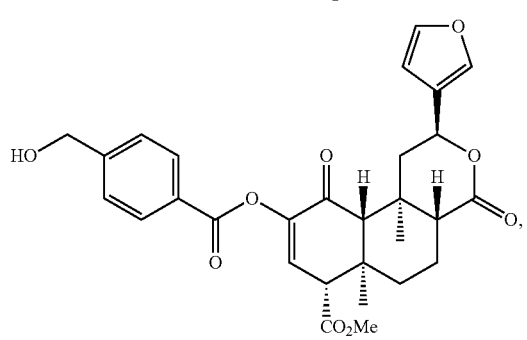
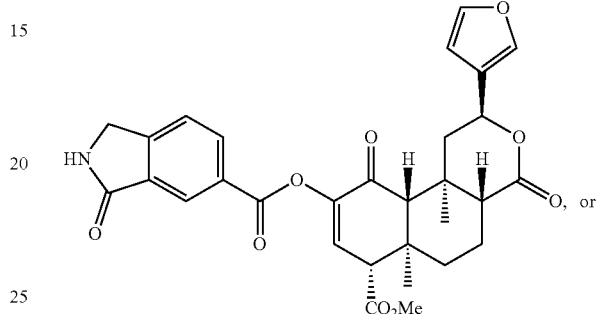
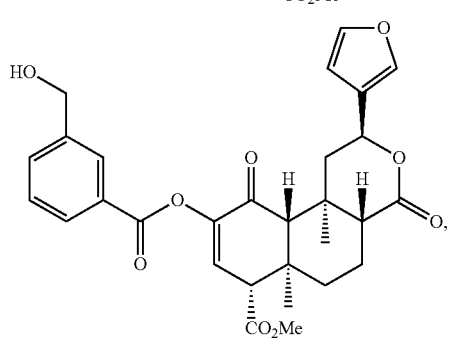
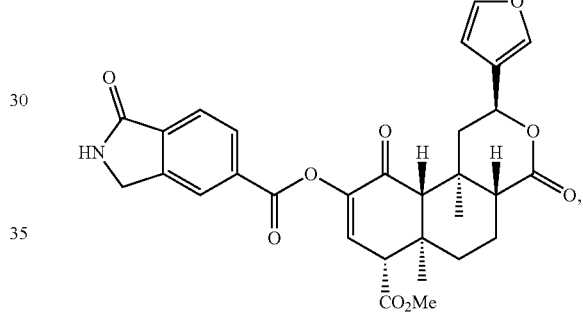
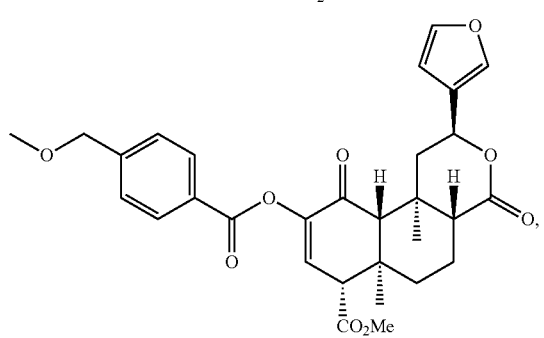
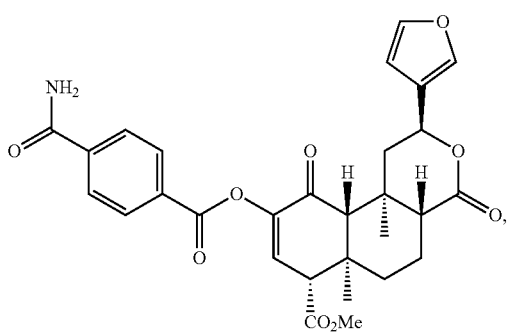

or a pharmaceutically acceptable salt and/or solvate thereof of any one of these.

In an aspect of the present technology, a composition is provided that includes any one of the herein-described embodiments of compounds of Formula I and a pharmaceutically acceptable carrier. In a related aspect, a pharmaceutical composition is provided, the pharmaceutical composition including an effective amount of the compound of any one of the aspects and embodiments of compounds of Formula I for treating pain in a subject; and a pharmaceutically acceptable carrier. In a further related aspect, a method is provided that includes administering an effective amount of a compound of any one of the embodiments of compounds of Formula I or administering a pharmaceutical composition including an effective amount of a compound of any one of the embodiments of compounds of Formula I to a subject suffering from pain.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of pain. The effective amount of the compound may selectively agonize the mu opioid receptor (MOR). The effective amount of the compound may selectively bind to the MOR at least about 5 times more than the δ opioid receptor (DOR); thus, the effective amount of the compound may selectively bind to the MOR at least about 10 times, at least about 25 times, at least about 50 times, or at least about 100 times more than the DOR. In any embodiment herein, including any of the above embodiments regarding the DOR, the effective amount of the compound may selectively bind to the MOR at least about 5 times more than the kappa opioid receptor (KOR); thus, it may be that the effective amount of the compound selectively binds to the MOR at least about 10 times more, at least 25 times more, at least about 50 times more, or at least about 100 times more than the KOR. As used herein, a "subject" or "patient" is a mammal, such as a cat, dog, rodent or primate. Typically the subject is a human, and, preferably, a human suffering from or suspected of suffering from pain. The term "subject" and "patient" can be used interchangeably.

Thus, the instant present technology provides pharmaceutical compositions and medicaments comprising any of the compounds disclosed herein (e.g., compounds of Formula I) and a pharmaceutically acceptable carrier or one or more excipients or fillers. The compositions may be used in the methods and treatments described herein. Such compositions and medicaments include a therapeutically effective amount of any compound as described herein, including but not limited to a compound of formula I. The pharmaceutical composition may be packaged in unit dosage form. The unit dosage form is effective in treating addiction by reducing desire for an addictive substance(s), and/or effective in treating a metabolic disorder by reducing symptoms associated with the metabolic disorder when administered to a subject in need thereof.

The pharmaceutical compositions and medicaments may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like. The compounds and compositions described herein may be used to prepare formulations and medicaments that prevent or treat pain. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or antioxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until, for example, the intensity of the pain decreases (e.g., as indicated by the patient). The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the pain and the pharmacological activity of the compound being used. The determination of optimum dosages for a particular patient is well known to those skilled in the art.

Various assays and model systems can be readily employed to determine the therapeutic effectiveness of the treatment according to the present technology. Effectiveness of the compositions and methods of the present technology may also be demonstrated by a decrease in the symptoms of pain, such as, for example, a decrease in movement and/or a decrease in response to external stimuli.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

The compounds of the present technology can also be administered to a patient along with other conventional therapeutic agents that may be useful in the treatment of pain. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially or synergistically be effective for the treatment of pain.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1\times10^{-4}$ g/kg to 1 g/kg, preferably, $1\times10^{-3}$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

In another aspect, the present technology provides methods of identifying a target of interest including contacting the target of interest with a detectable or imaging effective quantity of a labeled compound of the present technology. A detectable or imaging effective quantity is a quantity of a labeled compound of the present technology necessary to be detected by the detection method chosen. For example, a detectable quantity can be an administered amount sufficient to enable detection of binding of the labeled compound to a target of interest including, but not limited to, a MOR. Suitable labels are known by those skilled in the art and can include, for example, radioisotopes, radionuclides, isotopes, fluorescent groups, biotin (in conjunction with streptavidin complexation), and chemiluminescent groups. Upon binding of the labeled compound to the target of interest, the target may be isolated, purified and further characterized such as by determining the amino acid sequence.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

General Synthetic and Analytical Details:

Salvinorin A was isolated from the leaves of *Salvia divinorum* and converted to salvinorin B as previously described in Harding, W. W., Schmidt, M., Tidgewell, K., Kalman, P., Holden, K. G., Gilmour, B., Navarro, H., Rothman, R. B., and Prisinzano, T. E. (2006) Synthetic studies of neoclerodane diterpenes from *Salvia divinorum*: semisynthesis of salvinicins A and B and other chemical transformations of salvinorin A, *J. Nat. Prod.* 69, 107-112, incorporated herein by reference. All other chemical reagents were purchased from commercial suppliers and used without further purification. All solvents were obtained from a solvent purification system in which solvent was passed through two columns of activated alumina under argon. Reactions performed in standard glassware were performed under an atmosphere of argon using glassware dried overnight in an oven at 120° C. and cooled under a stream of argon. Reactions were monitored by thin-layer chromatography (TLC) on 0.25 mm Analtech GHLF silica gel plates and visualized using a UV Lamp (254 nm) and vanillin solution. Flash column chromatography was performed on silica gel (4-63 mm) from Sorbent Technologies. $^1$H and $^{13}$C NMR were recorded a 500 MHz Bruker AVIII spectrometer equipped with a cryogenically-cooled carbon observe probe or a 400 MHz Bruker AVIIIHD spectrometer using tetramethyl silane as an internal standard. Chemical shifts (δ) are reported in ppm and coupling constants (J) are reported in Hz. High-resolution mass spectrum (HRMS) was performed on a LCT Premier (Micromass Ltd., Manchester UK) time of flight mass spectrometer with an electrospray ion source in either positive or negative mode. Melting points were measured with a Thomas Capillary Melting Point Apparatus and are uncorrected. HPLC was carried out on an Agilent 1100 series HPLC system with diode array detection at 209 nm on an Agilent Eclipse XDB-C18 column (250×10 mm, 5 mm). Compounds were identified as ≥95% pure by HPLC before all in vitro and in vivo analyses.

Representative Synthetic Procedures for Representative Compounds of Study

Oxidation of Salvinorin B

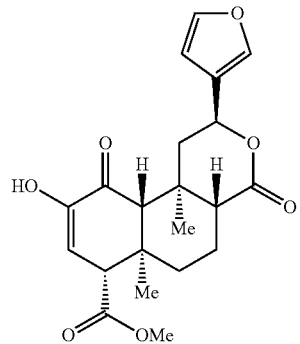

(2S,4aR,6aR,7R,10aR,10bR)-methyl 2-(furan-3-yl)-9-hydroxy-6a,10b-dimethyl-4,10-dioxo-2,4,4a,5,6,6a,7,10,10a,10b-decahydro-1H-benzo[f]isochromene-7-carboxylate (2)

A combination of CH$_2$Cl$_2$ (40 mL) and MeOH (40 mL) was added to a flask containing Salvinorin B (1, see Scheme 1 below) (250 mg, 0.640 mmol) and Cu(OAc)$_2$ (349 mg, 1.92 mmol). After stirring overnight at RT the reaction was concentrated in vacuo. The residue was redissolved in CH$_2$Cl$_2$ (40 mL) and H$_2$O (40 mL). The aqueous layer was reextracted with CH$_2$Cl$_2$ (2×40 mL). The combined organic layers were washed with saturated NH$_4$Cl (50 mL) and brine (50 mL) then dried over Na$_2$SO$_4$. The solvent was removed in vacuo and the residue purified via FCC eluting with 12.5% EtOAc/CH$_2$Cl$_2$ to yield 1 (43 mg, 17%) and an inseparable mixture of tautomers, herein represented by the indicated structure 2 (139 mg, 52%). $^1$H NMR (500 MHz, CDCl$_3$) δ 7.44 (m, 1H), 7.42 (m, 1H), 6.41 (dd, J=0.80, 1.79 Hz, 1H), 6.02 (d, J=2.50 Hz, 1H), 5.59 (dd, J=5.25, 11.62 Hz, 1H), 3.76 (s, 3H), 3.41 (d, J=2.49 Hz, 1H), 3.14 (dd, J=5.13, 13.35 Hz, 1H), 2.33 (s, 1H), 2.18 (m, 2H), 2.01 (m, 1H), 1.67 (m, 3H), 1.36 (s, 3H), 1.11 (s, 3H). 13C NMR (126 MHz, CDCl$_3$) δ 194.70, 171.32, 171.25, 146.69, 143.77, 139.38, 125.46, 112.18, 108.42, 71.92, 62.70, 55.98, 52.24, 51.27, 44.67, 43.88, 38.20, 35.78, 17.86, 16.64, 14.72. HRMS calculated for C$_{21}$H$_{24}$O$_7$: [M+Na]$^+$: 411.1409 (found); 411.1420 (calc). Melting point: 165-170° C. (dec).

Scheme 1.

(1)

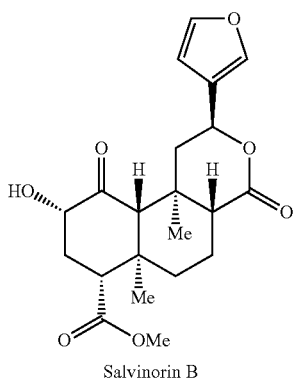

Salvinorin B

General Acylation Procedure.

An oven-dried flask was charged with 2 (40 mg, 0.103 mmol), EDC.HCl (29.5 mg, 0.154 mmol), DMAP (18.8 mg, 0.154 mmol), and the appropriate acid (0.154 mmol). To the flask was added CH$_2$Cl$_2$ (8 mL). After stirring overnight at RT the reaction was quenched with HCl (1 M, 8 mL) and the organic layer rinsed sequentially with saturated NaHCO$_3$ (8 mL) and brine (8 mL) then dried over Na$_2$SO$_4$. The solvent was removed in vacuo and the resulting residue purified by flash column chromatography ("FCC") eluting with 30-35% EtOAc/Pent. Compounds <95% pure as indicated by HPLC were further purified by reverse phase semi-preparatory HPLC.

Representative Compounds of Studies

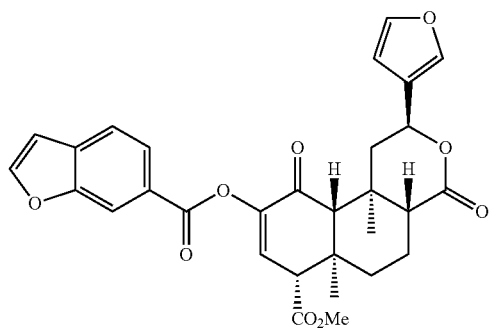

Methyl (2S,4aR,6aR,7R,10aR,10bR)-9-((benzo-furan-6-carbonyl)oxy)-2-(furan-3-yl)-6a,10b-dim-ethyl-4,10-dioxo-1,4,4a,5,6,6a,7,10,10a,10b-deca-hydro-2H-benzo[f]isochromene-7-carboxylate (3.44)

$^1$H NMR (500 MHz, CDCl$_3$) 8.28 (p, J=0.8 Hz, 1H), 8.01 (dd, J=8.2, 1.5 Hz, 1H), 7.80 (d, J=2.2 Hz, 1H), 7.68 (dd, J=8.2, 0.6 Hz, 1H), 7.49-7.36 (m, 2H), 6.85 (dd, J=2.2, 1.0 Hz, 1H), 6.68 (d, J=2.2 Hz, 1H), 6.39 (dd, J=1.9, 0.9 Hz, 1H), 5.60-5.46 (m, 1H), 3.81 (s, 3H), 3.61 (d, J=2.2 Hz, 1H), 3.08 (dd, J=13.7, 5.3 Hz, 1H), 2.49 (s, 1H), 2.26-2.17 (m, 1H), 2.13 (dt, J=13.2, 2.7 Hz, 1H), 1.79-1.58 (m, 2H), 1.39 (s, 3H), 1.26 (d, J=2.2 Hz, 5H). $^{13}$C NMR (126 MHz, CDCl$_3$) δ 190.96, 171.39, 170.40, 164.78, 154.30, 148.44, 145.52, 143.65, 139.36, 132.69, 129.94, 125.42, 124.74, 124.25, 121.15, 113.87, 108.45, 106.92, 72.07, 63.46, 56.51, 52.47, 51.38, 44.20, 43.80, 38.46, 35.85, 17.96, 16.84, 14.86. HRMS calculated for C$_{30}$H$_{28}$O$_9$ [M+H]$^+$: 533.1819 (found); 533.1806 (calcd). Melting point: 156-157° C. (decomp).

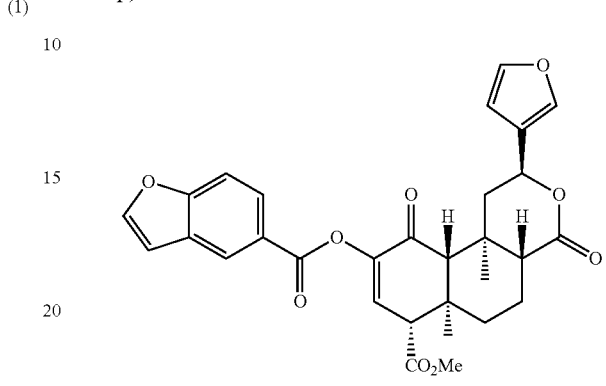

Methyl (2S,4aR,6aR,7R,10aR,10bR)-9-((benzo-furan-5-carbonyl)oxy)-2-(furan-3-yl)-6a,10b-dim-ethyl-4,10-dioxo-1,4,4a,5,6,6a,7,10,10a,10b-deca-hydro-2H-benzo[f]isochromene-7-carboxylate (3.45)

$^1$H NMR (500 MHz, CDCl$_3$) 8.46-8.40 (m, 1H), 8.08 (dd, J=8.7, 1.8 Hz, 1H), 7.71 (d, J=2.2 Hz, 1H), 7.57 (dt, J=8.7, 0.8 Hz, 1H), 7.48-7.34 (m, 2H), 6.86 (dd, J=2.2, 1.0 Hz, 1H), 6.68 (d, J=2.2 Hz, 1H), 6.39 (dd, J=2.0, 0.9 Hz, 1H), 5.62-5.47 (m, 1H), 3.80 (s, 3H), 3.61 (d, J=2.2 Hz, 1H), 3.08 (dd, J=13.7, 5.3 Hz, 1H), 2.49 (s, 1H), 2.20 (ddt, J=12.6, 6.9, 3.5 Hz, 2H), 2.12 (dt, J=13.1, 2.7 Hz, 1H), 1.79-1.63 (m, 3H), 1.39 (s, 3H), 1.25 (s, 3H). $^{13}$C NMR (126 MHz, CDCl$_3$) δ 191.04, 171.39, 170.42, 164.76, 157.96, 146.54, 145.52, 143.65, 139.36, 129.92, 127.66, 126.67, 125.41, 124.67, 123.18, 111.63, 108.45, 107.13, 72.06, 63.45, 56.51, 52.47, 51.38, 44.20, 43.80, 38.47, 35.85, 17.96, 16.84, 14.86. HRMS calculated for C$_{30}$H$_{28}$O$_9$ [M+H]$^+$: 533.1797 (found); 533.1806 (calcd). Melting point: 112-115° C.

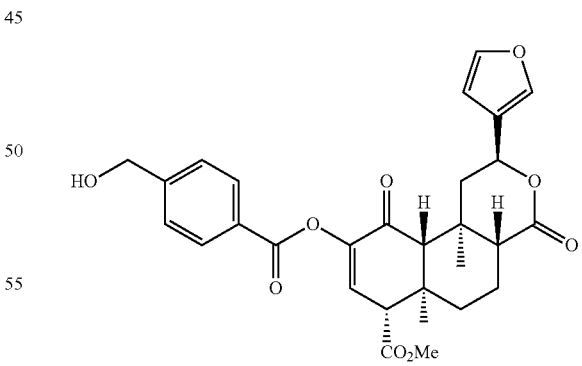

Methyl (2S,4aR,6aR,7R,10aR,10bR)-2-(furan-3-yl)-9-((4-(hydroxymethyl)benzoyl)oxy)-6a,10b-dim-ethyl-4,10-dioxo-1,4,4a,5,6,6a,7,10,10a,10b-deca-hydro-2H-benzo[f]isochromene-7-carboxylate (3.46)

4-(TBSOCH$_2$)benzoic acid was used in the acylation of 2 to provide a TBS-protected coupling product. To a flask containing the crude TBS-protected coupling product (0.2 mmol) was added a 1:1 mixture of MeOH and acetone (6 mL total) followed by a solution of KHSO$_4$ (0.1 mmol, 0.5 eq.) in 3 mL of H$_2$O. Reaction is a white suspension after water addition and was stirred overnight at r.t. Upon reaction completion, as monitored by TLC, the solvent was evaporated and the product was extracted from water (10 mL) into EtOAc (3×10 mL). The combined organic layers were washed with brine, dried over Na$_2$SO$_4$, and solvent was removed. The compound was purified by FCC (50% EtOAc/Pentane). $^1$H NMR (500 MHz, CDCl$_3$) 8.14-8.02 (m, 2H), 7.48 (d, J=8.3 Hz, 2H), 7.45-7.36 (m, 2H), 6.66 (d, J=2.2 Hz, 1H), 6.39 (dd, J=1.9, 0.9 Hz, 1H), 5.54 (dd, J=11.5, 5.3 Hz, 1H), 4.80 (d, J=2.6 Hz, 2H), 3.80 (s, 3H), 3.60 (d, J=2.3 Hz, 1H), 3.06 (dd, J=13.7, 5.3 Hz, 1H), 2.47 (s, 1H), 2.24-2.16 (m, 2H), 2.12 (dt, J=13.4, 2.7 Hz, 1H), 1.90 (s, 1H), 1.77-1.64 (m, 3H), 1.37 (s, 3H), 1.24 (s, 3H). $^{13}$C NMR (126 MHz, CDCl$_3$) δ 190.90, 171.40, 170.39, 164.40, 147.14, 145.42, 143.66, 139.37, 130.53, 129.99, 127.37, 126.55, 125.40, 108.44, 72.06, 64.57, 63.44, 56.49, 52.48, 51.36, 44.19, 43.79, 38.45, 35.84, 17.94, 16.82, 14.85. HRMS calculated for C$_{29}$H$_{30}$O$_9$ [M+H]$^+$: 523.1964 (found); 523.1963 (calcd). Melting point: 115-118° C.

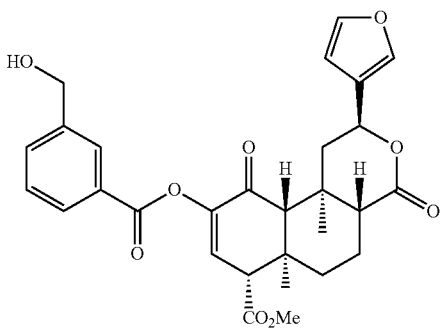

Methyl (2S,4aR,6aR,7R,10aR,10bR)-2-(furan-3-yl)-9-((3-(hydroxymethyl)benzoyl)oxy)-6a,10b-dimethyl-4,10-dioxo-1,4,4a,5,6,6a,7,10,10a,10b-decahydro-2H-benzo[f]isochromene-7-carboxylate (3.47)

3-(TBSOCH$_2$)benzoic acid was used in the acylation of 2 to provide a TBS-protected coupling product. To a flask containing the crude TBS-protected coupling product (0.2 mmol) was added a 1:1 mixture of MeOH and acetone (6 mL total) followed by a solution of KHSO$_4$ (0.1 mmol, 0.5 eq.) in 3 mL of H$_2$O. Reaction is a white suspension after water addition and was stirred overnight at r.t. Upon reaction completion, as monitored by TLC, the solvent was evaporated and the product was extracted from water (10 mL) into EtOAc (3×10 mL). The combined organic layers were washed with brine, dried over Na$_2$SO$_4$, and solvent was removed. The compound was purified by FCC (50% EtOAc/Pentane). $^1$H NMR (500 MHz, CDCl$_3$) 8.11 (d, J=1.7 Hz, 1H), 8.03 (d, J=7.8 Hz, 1H), 7.64 (d, J=7.6 Hz, 1H), 7.48 (t, J=7.7 Hz, 1H), 7.43-7.37 (m, 2H), 6.66 (d, J=2.1 Hz, 1H), 6.39 (d, J=1.8 Hz, 1H), 5.54 (dd, J=11.5, 5.3 Hz, 1H), 4.77 (s, 2H), 3.80 (s, 3H), 3.60 (d, J=2.1 Hz, 1H), 3.06 (dd, J=13.7, 5.4 Hz, 1H), 2.47 (s, 1H), 2.24-2.07 (m, 3H), 1.85 (s, 1H), 1.77-1.63 (m, 3H), 1.37 (s, 3H), zj1.24 (s, 3H). $^{13}$C NMR (126 MHz, CDCl$_3$) δ 190.87, 171.38, 170.37, 164.47, 145.45, 143.67, 141.56, 139.38, 132.31, 129.98, 129.49, 128.90, 128.56, 128.52, 125.44, 108.45, 72.06, 64.63, 63.49, 56.51, 52.46, 51.38, 44.22, 43.82, 38.48, 35.86, 17.97, 16.82, 14.86. HRMS calculated for C$_{29}$H$_{30}$O$_9$ [M+H]$^+$: 523.1959 (found); 523.1963 (calcd). Melting point: 104-106° C.

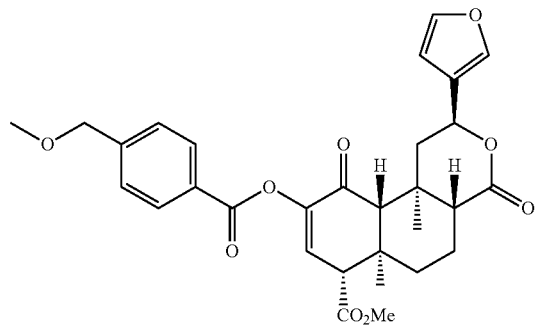

Methyl (2S,4aR,6aR,7R,10aR,10bR)-2-(furan-3-yl)-9-((4-(methoxymethyl)benzoyl)oxy)-6a,10b-dimethyl-4,10-dioxo-1,4,4a,5,6,6a,7,10,10a,10b-decahydro-2H-benzo[f]isochromene-7-carboxylate (3.48)

$^1$H NMR (500 MHz, CDCl$_3$) 8.17-8.00 (m, 2H), 7.47-7.43 (m, 2H), 7.41 (dd, J=1.6, 0.9 Hz, 1H), 7.39 (t, J=1.7 Hz, 1H), 6.66 (d, J=2.1 Hz, 1H), 6.39 (dd, J=1.9, 0.9 Hz, 1H), 5.60-5.48 (m, 1H), 4.54 (s, 2H), 3.80 (s, 3H), 3.60 (d, J=2.3 Hz, 1H), 3.42 (s, 3H), 3.07 (dd, J=13.7, 5.3 Hz, 1H), 2.47 (s, 1H), 2.20 (ddd, J=12.2, 6.4, 3.1 Hz, 2H), 2.12 (dt, J=13.1, 2.7 Hz, 1H), 1.80-1.62 (m, 3H), 1.38 (s, 3H), 1.24 (s, 3H). $^{13}$C NMR (126 MHz, CDCl$_3$) δ 190.90, 171.38, 170.38, 164.42, 145.43, 144.74, 143.66, 139.36, 130.42, 129.97, 127.42, 127.28, 125.41, 108.44, 73.90, 72.05, 63.45, 58.45, 56.49, 52.47, 51.37, 44.19, 43.80, 38.45, 35.84, 17.95, 16.82, 14.85. HRMS calculated for C$_{30}$H$_{32}$O$_9$ [M+Na]$^+$: 559.1922 (found); 559.1944 (calcd). Melting point: 135-140° C.

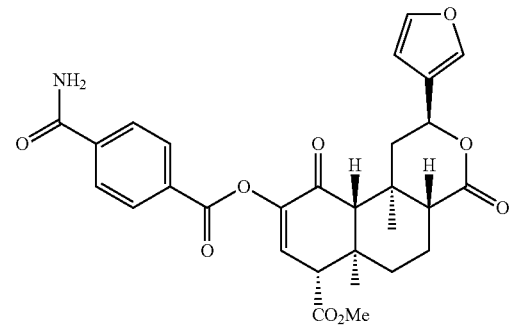

Methyl (2S,4aR,6aR,7R,10aR,10bR)-9-((4-carbamoylbenzyl)oxy)-2-(furan-3-yl)-6a,10b-dimethyl-4,10-dioxo-1,4,4a,5,6,6a,7,10,10a,10b-decahydro-2H-benzo[f]isochromene-7-carboxylate (3.49)

$^1$H NMR (500 MHz, CDCl$_3$) 8.26-8.09 (m, 2H), 7.96-7.84 (m, 2H), 7.47-7.30 (m, 2H), 6.70 (d, J=2.2 Hz, 1H), 6.39 (dd, J=1.9, 0.9 Hz, 1H), 6.11 (d, J=21.1 Hz, 1H), 5.67 (s, 1H), 5.55 (dd, J=11.6, 5.5 Hz, 1H), 3.81 (s, 3H), 3.80 (s, 1H), 3.61 (d, J=2.2 Hz, 1H), 3.06 (dd, J=13.7, 5.3 Hz, 1H), 2.48 (s, 1H), 2.26-2.14 (m, 2H), 2.16-2.09 (m, 1H), 1.46 (s,

1H), 1.38 (s, 3H), 1.35 (s, 1H), 1.25 (s, 3H). $^{13}$C NMR (126 MHz, CDCl$_3$) δ 190.73, 171.45, 170.31, 167.89, 163.67, 145.28, 143.70, 139.37, 137.95, 131.36, 130.58, 130.26, 127.60, 125.38, 108.43, 72.02, 63.48, 56.47, 52.53, 51.36, 44.25, 43.81, 38.45, 35.86, 17.94, 16.83, 14.86. HRMS calculated for C$_{29}$H$_{30}$NO$_9$ [M+Na]$^+$: 558.1728 (found); 558.1740 (calcd). Melting point: 201-203° C.

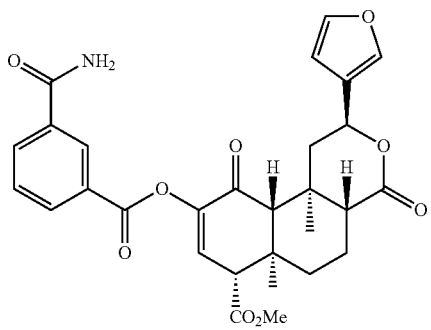

Methyl (2S,4aR,6aR,7R,10aR,10bR)-9-((3-carbamoylbenzyl)oxy)-2-(furan-3-yl)-6a,10b-dimethyl-4,10-dioxo-1,4,4a,5,6,6a,7,10,10a,10b-decahydro-2H-benzo[f]isochromene-7-carboxylate (3.50)

$^1$H NMR (500 MHz, CDCl$_3$) 8.51 (dt, J=4.1, 1.7 Hz, 1H), 8.25 (ddt, J=7.8, 3.2, 1.4 Hz, 1H), 8.14 (dq, J=7.8, 1.4 Hz, 1H), 7.59 (td, J=7.8, 1.5 Hz, 1H), 7.44-7.36 (m, 2H), 6.68 (d, J=2.2 Hz, 1H), 6.54-6.40 (m, 1H), 6.38 (dt, J=1.8, 0.9 Hz, 1H), 6.19-5.99 (m, 1H), 5.53 (ddd, J=13.2, 8.3, 5.4 Hz, 1H), 3.80 (d, J=4.1 Hz, 3H), 3.62 (d, J=2.2 Hz, 1H), 3.04 (td, J=13.5, 12.9, 5.3 Hz, 1H), 2.50 (s, 1H), 2.20 (ddd, J=16.0, 9.1, 3.2 Hz, 2H), 2.12 (dd, J=13.3, 3.6 Hz, 1H), 1.81-1.62 (m, 2H), 1.44 (s, 1H), 1.36 (s, 3H), 1.23 (s, 3H). $^{13}$C NMR (126 MHz, CDCl$_3$) δ 190.82, 171.43, 170.35, 168.05, 163.77, 145.24, 143.68, 139.40, 133.96, 133.46, 133.07, 130.31, 129.21, 128.84, 128.70, 125.35, 108.44, 72.02, 63.34, 56.40, 52.52, 51.26, 44.24, 43.71, 38.40, 35.82, 17.93, 16.82, 14.84. HRMS calculated for C$_{29}$H$_{30}$NO$_9$ [M+Na]$^+$: 558.1754 (found); 558.1740 (calcd). Melting point: 199-201° C.

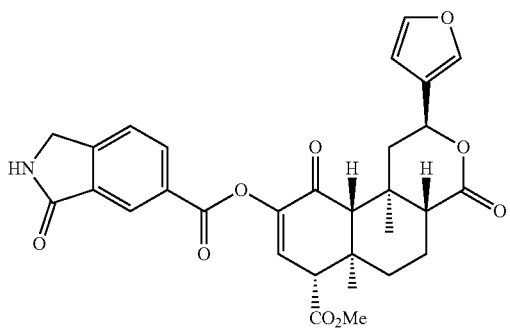

(2S,4aR,6aR,7R,10aR,10bR)-2-(furan-3-yl)-7-(methoxycarbonyl)-6a,10b-dimethyl-4,10-dioxo-1,4,4a,5,6,6a,7,10,10a,10b-decahydro-2H-benzo[f]isochromen-9-yl 3-oxoisoindoline-5-carboxylate (3.51)

$^1$H NMR (500 MHz, CDCl$_3$) 8.69-8.56 (m, 1H), 8.31 (ddd, J=7.9, 2.8, 1.6 Hz, 1H), 7.61 (dd, J=7.9, 0.9 Hz, 1H), 7.55 (s, 1H), 7.42 (ddt, J=2.6, 1.8, 0.8 Hz, 1H), 7.39 (t, J=1.7 Hz, 1H), 6.70 (d, J=2.2 Hz, 1H), 6.39 (dd, J=1.9, 0.9 Hz, 1H), 5.58-5.51 (m, 1H), 4.56 (d, J=2.7 Hz, 2H), 3.81 (s, 2H), 3.62 (d, J=2.2 Hz, 1H), 3.06 (dd, J=13.8, 5.5 Hz, 1H), 2.49 (s, 1H), 2.25-2.17 (m, 2H), 2.16-2.08 (m, 1H), 2.01 (s, 1H), 1.84-1.61 (m, 3H), 1.38 (s, 3H), 1.25 (s, 3H). $^{13}$C NMR (126 MHz, CDCl$_3$) δ 190.72, 171.39, 170.54, 170.30, 163.77, 148.90, 145.30, 143.67, 139.36, 133.48, 132.80, 130.23, 128.75, 126.06, 125.40, 123.69, 108.44, 72.04, 63.41, 56.43, 52.50, 51.32, 45.89, 44.22, 43.75, 38.40, 35.85, 17.94, 16.81, 14.84. HRMS calculated for C$_{30}$H$_{29}$O$_9$N [M+H]$^+$: 548.1910 (found); 548.19151 (calcd). Melting point: 189-194° C.

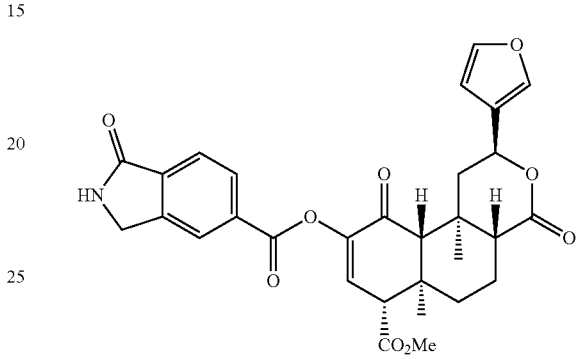

(2S,4aR,6aR,7R,10aR,10bR)-2-(furan-3-yl)-7-(methoxycarbonyl)-6a,10b-dimethyl-4,10-dioxo-1,4,4a,5,6,6a,7,10,10a,10b-decahydro-2H-benzo[f]isochromen-9-yl 1-oxoisoindoline-5-carboxylate (3.52)

$^1$H NMR (500 MHz, CDCl$_3$) 8.26-8.19 (m, 2H), 7.97 (d, J=8.3 Hz, 1H), 7.60 (s, 1H), 7.45-7.25 (m, 3H), 6.71 (d, J=2.1 Hz, 1H), 6.39 (dd, J=2.0, 0.9 Hz, 1H), 5.54 (dd, J=11.5, 5.4 Hz, 1H), 4.54 (s, 2H), 3.81 (s, 3H), 3.62 (d, J=2.2 Hz, 1H), 3.07 (td, J=13.5, 6.8 Hz, 1H), 2.50 (s, 1H), 2.20 (td, J=11.5, 10.0, 4.7 Hz, 2H), 2.14-2.09 (m, 1H), 2.01 (s, OH), 1.76 (ddd, J=14.3, 10.7, 5.4 Hz, 2H), 1.69 (d, J=13.1 Hz, 1H), 1.38 (s, 3H), 1.25 (s, 3H). $^{13}$C NMR (126 MHz, CDCl$_3$) δ 190.79, 171.32, 170.48, 170.32, 163.90, 145.27, 143.69, 143.57, 139.37, 136.85, 131.43, 130.30, 130.20, 125.37, 125.31, 124.05, 108.43, 72.00, 63.42, 56.43, 52.53, 51.31, 45.65, 44.26, 43.76, 38.42, 35.85, 17.93, 16.82, 14.84. HRMS calculated for C$_{30}$H$_{29}$O$_9$N [M+NH$_4$]$^+$: 565.2198 (found); 565.2186 (calcd). Melting point: 229-232° C.

In Vitro Pharmacology

Cell culture and opioid receptor agonist activity assays proceeded as described in Riley, A. P., Groer, C. E., Young, D., Ewald, A. W., Kivell, B. M., and Prisinzano, T. E. (2014) Synthesis and kappa-opioid receptor activity of furan-substituted salvinorin A analogues, J. Med. Chem. 57, 10464-10475 (incorporated herein by reference in its entirety for any and all purposes).

β-Arrestin-2 EFC Recruitment Assay.

The effect on β-arrestin-2 recruitment was evaluated using methods as described in Crowley, R. S.; Riley, A. P.; Sherwood, A. M.; Groer, C. E.; Shivaperumal, N.; Biscaia, M.; Paton, K.; Schneider, S.; Provasi, D.; Kivell, B. M.; Filizola, M.; Prisinzano, T. E. (2016) Synthetic studies of neoclerodane diterpenes from Salvia divinorum: identification of a potent and centrally acting μ opioid analgesic with reduced abuse liability. J. Med. Chem. 59, 11027-11038 (incorporated herein by reference in its entirety for any and all purposes). Briefly, on day 1, ~80% confluent CHO-K1 OPRM1 β-arrestin-2 cells were detached from culture plates using nonenzymatic cell dissociation buffer (Life Technologies, Thermo Fisher Scientific, Waltham, Mass.) and counted using a hemocytometer. Cells were plated at 5000 cells/well in 20 µL of Cell Plating Reagent 2 (DiscoveRx, Fremont, Calif.) in 384-well tissue culture plates and incubated at 37° C. overnight. On day 2, stock solutions of test compounds were generated in 100% DMSO to 5 mM. The stock solutions were used to make 11 serial dilutions and then diluted to yield 5× compound concentrations in assay buffer (Hank's Balanced Salt Solution [HBSS, Life Technologies] with 10 mM HEPES [Life Technologies]). The cells were treated with 5 µL of the test compound solutions, final concentration of 1× compound, and 1% DMSO. Cells were incubated for 90 min at 37° C. Cells were then treated with detection reagents, 12.5 µL per well, according to manufacturer's instructions and incubated at room temperature for at least 1 h protected from light. Luminescence was quantified using a Synergy 2 plate reader with Gen5 Software (BioTek, Winooski, Vt.). Data were normalized to vehicle (no compound, 1% DMSO final concentration) to remove any background luminescence. The highest dose(s) of DAMGO was used as 100% recruitment, and all data was converted to percentages based upon the DAMGO response. Bias factors were calculated according to Equation 1, provided below:

$$\log(\text{Bias Factor}) = \left(\log\left(\frac{\text{Emax}_{test} \times EC50_{DAMGO}}{EC50_{test} \times \text{Emax}_{DAMGO}}\right)\right)_{\beta-arrestin} - \left(\log\left(\frac{\text{Emax}_{test} \times EC50_{DAMGO}}{EC50_{test} \times \text{Emax}_{DAMGO}}\right)\right)_{cAMP} \quad \text{Eq. 1}$$

In Vivo Methods Details

Animal Studies.

Adult male B6-SJL mice (22-29 g) and male Sprague Dawley rats (240-350 g) were housed on a 12 h light cycle and experiments were conducted during the light cycle. All animals were bred and housed at the Victoria University of Wellington (VUW) small animal facility, New Zealand. All experimental procedures were approved by the VUW Animal Ethics Committee and carried out in accordance to their guidelines for animal care. Food and water were provided ad libitum except during experimental procedures.

Hot Water Tail-Flick Dose-Dependent Antinociceptive Effects:

To determine dose-dependent anti-nociceptive effects, the cumulative dose response will be carried out in mice following repeated subcutaneous (s.c.) injections in the as described in Bohn, L. M., Lefkowitz, R. J., Gainetdinov, R. R., Peppel, K., Caron, M. G., and Lin, F. T. (1999) "Enhanced morphine analgesia in mice lacking beta-arrestin 2", Science 286, 2495-2498 (incorporated herein by reference in its entirety for any and all purposes). Withdrawal latencies will be measured 30 min following each dose. $ED_{50}$ values will be calculated by non-linear regression analysis from each individual curve using GraphPad Prism.

Hot Water Tail-Flick Tolerance Evaluation:

To measure the effect of tolerance, compounds were administered to mice daily for 9 days as described in Bohn, L. M., Gainetdinov, R. R., Lin, F.-T., Lefkowitz, R. J., and Caron, M. G. (2000) "[mu]-Opioid receptor desensitization by [beta]-arrestin-2 determines morphine tolerance but not dependence," Nature 408, 720-723 (incorporated herein by reference in its entirety for any and all purposes). Tail flick latencies were measured 30 min following administration on days 1, 3, 5, 7 and 9. Mice given daily vehicle treatments were challenged with either morphine or compound 3.46 on day 9 to show the prolonged exposure to the hot water tail immersion did not change the analgesic effects when compared to day 1.

Accelerating Rotarod Performance Assay.

Motor incoordination will be assessed in mice using an accelerating rotarod protocol using previously described methods, such as Deacon, R. M. (2013) "Measuring motor coordination in mice," Journal of visualized experiments: JoVE, e2609 (incorporated herein by reference in its entirety for any and all purposes). Mice will be initially trained on the rotarod apparatus (Harvard Apparatus, MA, USA, 32 mm diameter) in 16 sessions over a 4 day period. An accelerating procedure (4-40 rpm) with a 300 s cut-off will be used. Latencies will be measured as the time taken for the animal to fall off the apparatus. On the test day, initial baseline latencies for each animal will be measured in triplicate. Animals which are unable to consistently stay on the apparatus for at least 240 s will be excluded from the experiment. Following administration of a compound of the present technology, morphine (10 mg/kg, i.p.), or vehicle the latency to fall from the apparatus will be measured at 15, 30, 45, 60, 90, 120, 180 and 240 min. The percentage baseline will be calculated at each time point by the equation: % baseline=(test latency/baseline latency)×100.

Conditioned Place Preference Assay.

The conditioned place preference will be evaluated using methods as described in Piepponen, T. P., Kivastik, T., Katajamaki, J., Zharkovsky, A., and Ahtee, L. (1997) Involvement of opioid mu 1 receptors in morphine-induced conditioned place preference in rats, Pharmacol. Biochem. Behav. 58, 275-279 (incorporated herein by reference in its entirety for any and all purposes). Briefly, on habituation day (day 1) adult male Sprague Dawley rats (240-350 g) will be allowed to freely explore the 3-chambered place preference apparatus (PanLab Harvard Apparatus) for 15 min to determine baseline preference using Smart 3.0 software (PanLab). Animals exhibiting preference in the outer compartments (30×30×34 cm) of over 80% or over 40% in the central corridor (8×10×34 cm) will be considered exclusions. Conditioning will be carried out on days 2-7 for 60 min with drug treatment (5 or 10 mg/kg, i.p.) paired to the least preferred outer compartment and vehicle (DMSO: Polyethylene glycol at a ratio of 1:3 i.p) administered to the preferred chamber in a counterbalanced design. On test day (day 8) conditioned preference will be determined in a single 15 min trial with free access to the entire apparatus. Results will be reported as the difference in the times spent on the drug-paired side versus the vehicle-paired side and One-way ANOVA with Bonferroni's multiple comparisons tests used to determine statistical significance.

Representative Results

An in vitro comparison of representative compounds of the present technology to kurkinorin was performed using a commercially available functional assay that measures forskolin-induced cAMP accumulation in CHO cells stably expressing MOR, where the results are provided in Table 1.

TABLE 1

MOR Potencies of Compounds of Present Technology vs. Kurkinorin.

[Core structure: tricyclic scaffold with 3-furyl group, methyl ester, and G²-carbonate substituent]

| Entry | G² = | EC₅₀ (nM)$^{a,b}$ |
|---|---|---|
| kurkinorin | phenyl | 1.2 ± 0.2 |
| 1 | benzofuran-6-yl | 1.5 ± 0.6 |
| 2 | benzofuran-5-yl | 9 ± 2 |
| 3 | 4-(hydroxymethyl)phenyl | 0.03 ± 0.01 |
| 4 | 3-(hydroxymethyl)phenyl | 2.42 ± 0.07 |
| 5 | 4-(methoxymethyl)phenyl | 13 ± 3 |
| 6 | 4-carbamoylphenyl | 0.19 ± 0.03 |
| 7 | 3-carbamoylphenyl | >10,000$^c$ |
| 8 | 3-oxoisoindolin-5-yl | 2.2 ± 0.2 |
| 9 | 3-oxoisoindolin-6-yl | 3.2 ± 0.7 |

$^a$EC₅₀ = Effective concentration to produce 50% of the maximal response as measured by inhibition of cAMP accumulation in CHO cells expressing MOR.
$^b$E$_{max}$ = 100%, unless otherwise noted.
$^c$E$_{max}$ = 0%.

These results show that representative compounds of the present technology are potent MOR agonists, where the compound of entry 6 (compound 3.49) is almost an order of magnitude more potent than kurkinorin, and the compound of entry 3 (compound 3.46) is about two orders of magnitude more potent than kurkinorin. Notably, testing showed that each of the compounds of the present technology from Table 1 exhibit EC₅₀ values for KOR>10,000 nM—thus, the compounds of the present technology are highly selective for agonizing MOR over KOR.

Figure 1B:
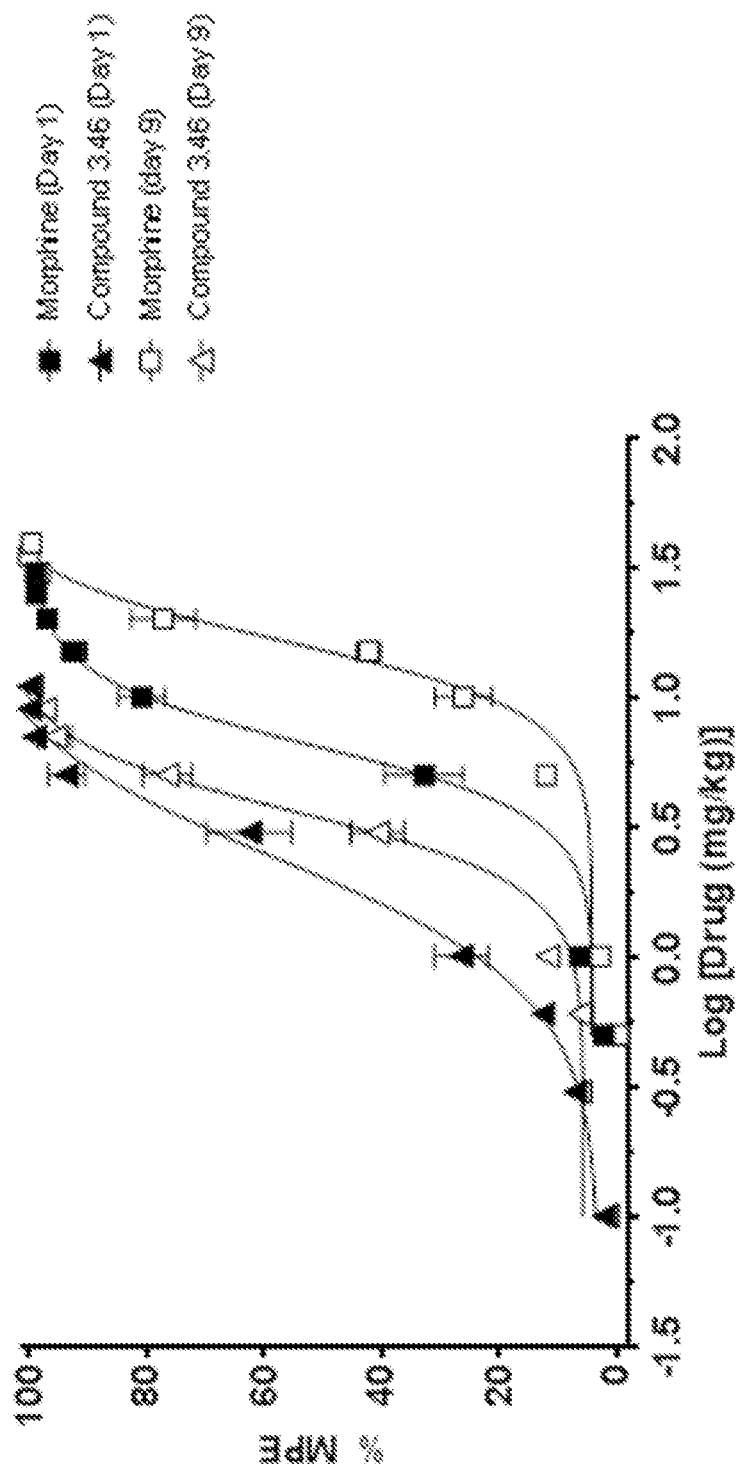

Antinociceptive effects in the hot water tail-flick assay in mice were examined, where the results following daily administration of dosages of the compounds that provided max effect (10 mg/kg/i.p. morphine or 5 mg/kg/i.p. compound 3.46) are provided in FIGS. 1A & 1B (n=4). Data shown in FIGS. 1A-B are mean±SEM. As illustrated by FIG. 1A, morphine showed significant antinociceptive effects (expressed in % maximal possible effect) on days 1 and 3 but not day 9. FIG. 1B further illustrates the change in antinoceptive effect of morphine on day 9 compared to day 1. However, compound 3.46 surprisingly maintained antinociceptive efficacy from days 1-9 (FIGS. 1A-AB). Daily vehicle treated mice display no antinociceptive effects days 1-9 (see FIG. 1A).

Figure 2A:
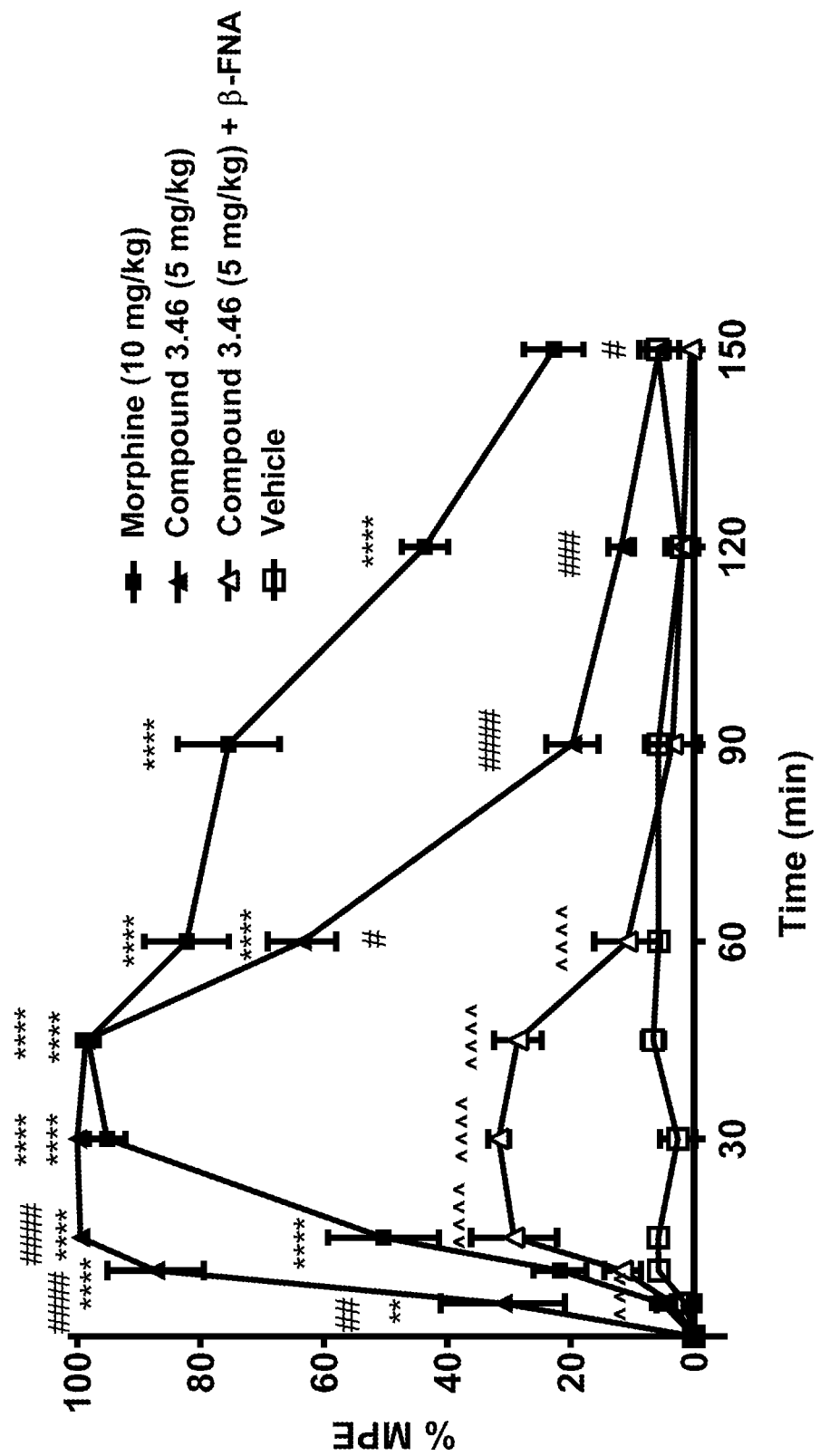
FIGS. 2A-B compare the results of a hot water tail-flick assay in mice that received a single i.p. injection of (a) 10 mg/kg morphine, (b) 5 mg/kg compound 3.46, (c) 5 mg/kg compound 3.46 following pre-administration of beta-funaltrexamine ("β-FNA"; 5 mg/kg, s.c), and (d) vehicle.
Figure 2B:
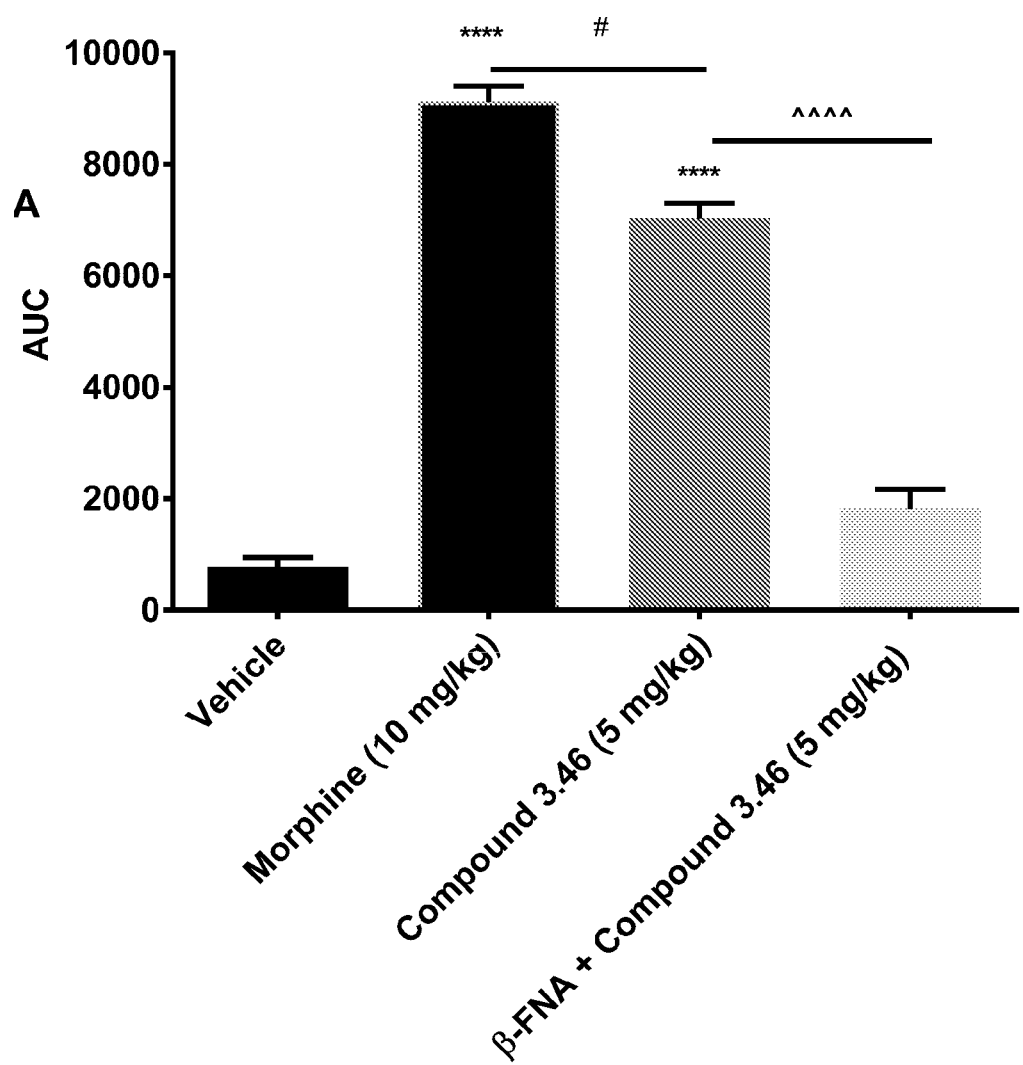

FIGS. 2A-B compare the results of a hot water tail-flick assay in mice that received a single i.p. injection of (a) 10 mg/kg morphine, (b) 5 mg/kg compound 3.46, (c) 5 mg/kg compound 3.46 following pre-administration of beta-funaltrexamine ("β-FNA"; 5 mg/kg, s.c), and (d) vehicle. FIG. 2A provides the time course of analgesic effects in the hot water tail-flick assay and FIG. 2B provides an area under the curve ("AUC") analysis, where p<0.01, *p<0.001, ****p<0.0001, drug compared to vehicle, #p<0.05, ##p<0.01, ###p<0.001, ####p<0.0001 compared to morphine, ^^^^p<0.0001 3.46 compared to 3.46+β-FNA. Data shown as mean±SEM (N=5-7 per group).

It is expected that compounds of the present technology (e.g., compound 3.46) will exhibit less or essentially no decrease in motor coordination as compared to morphine. For example, preliminary data in the accelerating rotarod performance assay shows administration of compound 3.46 exhibits significantly less effects on motor coordination than morphine. It is expected that compounds of the present technology (e.g., compound 3.46) will exhibit essentially the same effects as vehicle in the conditioned place preference assay as contrasted with morphine. It is expected that compounds of the present technology (e.g., compound 3.46) will show a significant decrease in preference compared to morphine and rewarding effects will not be significantly different form vehicle.

An in vitro comparison of representative compounds of the present technology to DAMGO, morphine, and fentanyl was performed using a commercially available functional assay that measures β-arrestin-2 recruitment in CHO-K1 OPRM1 cells stably expressing a fusion protein of β-arrestin-2 and a mutant β-galactosidase, where the results are provided in Table 2.

TABLE 2

MOR Potencies of Compounds of Present Technology vs. DAMGO.

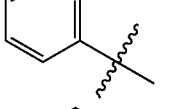

| Entry | $G^2$ = | $EC_{50} \pm SEM^a$ (nM) (% Efficacy)$^b$ | Bias Factor |
|---|---|---|---|
| DAMGO | Not Applicable | 42 ± 5 (97) | 1.0 |
| morphine | Not Applicable | 380 ± 40 (38) | 0.36 |
| fentanyl | Not Applicable | 38 ± 2 (70) | 0.34 |
| kurkinorin | Not Applicable | 140 ± 40 (96) | 0.57 |
| 1 | 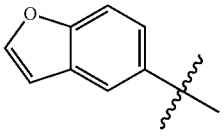 [SMILES: *c1ccc2occc2c1] | 40 ± 10 (90) | 2.62 |
| 2 | 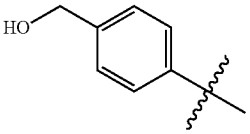 [SMILES: *c1ccc(CO)cc1] | 490 ± 80 (84) | 1.21 |
| 3 | 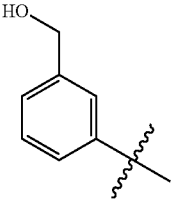 | 14 ± 1 (81) | 0.14 |
| 4 | 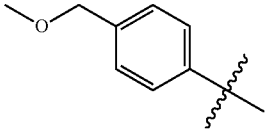 [SMILES: *c1ccc(COC)cc1] | 150 ± 30 (75) | 0.87 |
| 5 | 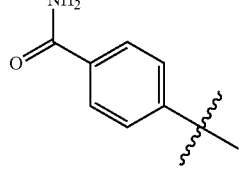 | 360 ± 80 (74) | 1.98 |
| 6 | 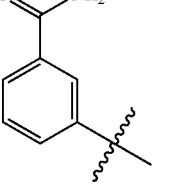 | 10 ± 3 (119) | 1.57 |
| 7 |  | >25000 (0) | — |

TABLE 2-continued

MOR Potencies of Compounds of Present Technology vs. DAMGO.

| Entry | G² = | EC₅₀ ± SEM$^a$ (nM) (% Efficacy)$^b$ | Bias Factor$^c$ |
|---|---|---|---|
| 8 | (isoindolinone-HN-C(=O)- substituent) | 190 ± 60 (76) | 0.65 |
| 9 | (isoindolinone substituent) | 260 ± 60 (88) | 0.81 |

$^a$Mean ± standard error of the mean; n ≥ 3 individual experiments run in triplicate.
$^b$Maximum efficacy values calculated based on DAMGO maximum stimulation.
$^c$Bias factors were calculated using Eq. 1.
Values <1 indicate bias towards the cAMP pathway and values >1 indicate bias towards the β-arrestin-2 pathway.
DAMGO is the reference compound, with a bias = 1.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound of Formula I:

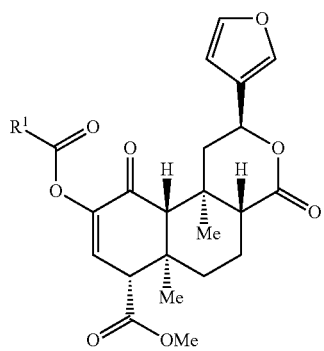

(I)

or a pharmaceutically acceptable salt and/or solvate thereof, wherein

R$^1$ is

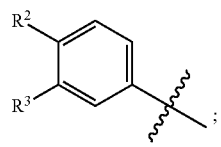

R$^2$ is a substituted C$_1$-C$_3$ alkyl, —C(O)H, —C(O)—C$_1$-C$_3$ alkyl, or —C(O)—NR$^4$R$^5$, and
R$^3$ is H, halo, substituted C$_1$-C$_3$ alkyl, or C$_1$-C$_3$ alkoxy;
or
R$^2$ and R$^3$ combined are heterocyclyl or heteroaryl; and
R$^4$ and R$^5$ are each independently H or C$_1$-C$_3$ alkyl.

B. The compound of Paragraph A, wherein
R$^2$ is a hydroxyl-substituted C$_1$-C$_3$ alkyl, a C$_1$-C$_3$ alkoxy substituted C$_1$-C$_3$ alkyl, —C(O)—C$_1$-C$_3$ alkyl, or —C(O)—NR$^4$R$^5$.

C. The compound of Paragraph A or Paragraph B, wherein R$^2$ is hydroxymethyl, (R)-1-hydroxyethyl, (S)-1-hydroxyethyl, methoxymethyl, or —C(O)—NH$_2$.

D. The compound of any one of Paragraphs A-C, wherein R$^3$ is H or R$^2$ and R$^3$ combined are heterocyclyl or heteroaryl.

E. The compound of any one of Paragraphs A-D, wherein when R$^2$ and R$^3$ are combined, R$^1$ is

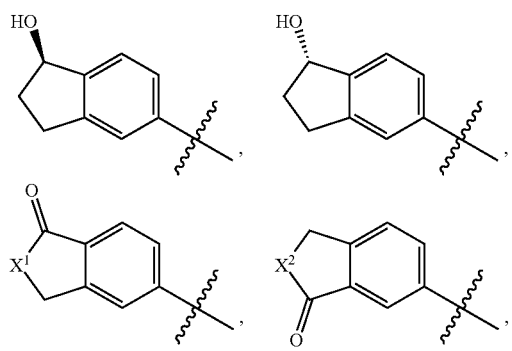

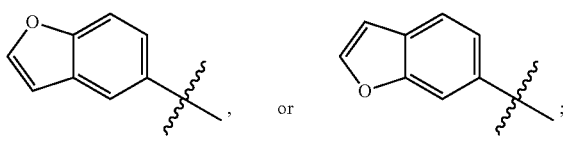

wherein X$^1$ and X$^2$ are each independently CH$_2$, O, or NH.

F. The compound of any one of Paragraphs A-E, wherein the compound is

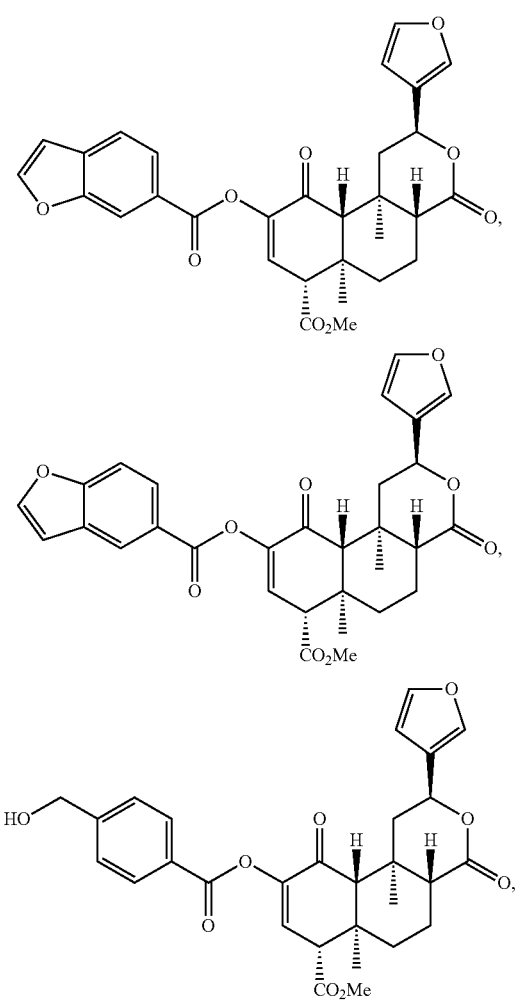

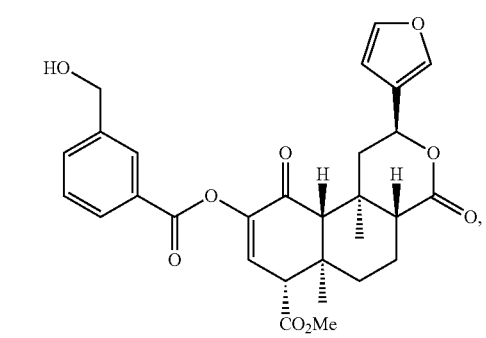

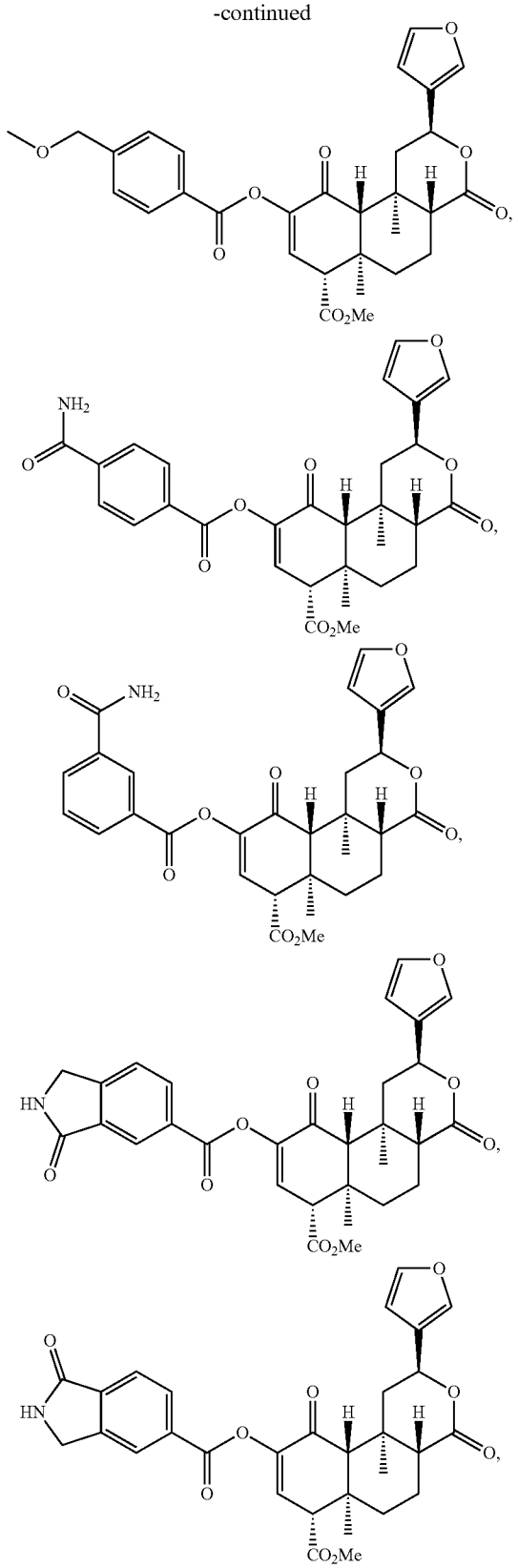

G. A composition comprising the compound of any one of Paragraphs A-F and a pharmaceutically acceptable carrier.

H. A pharmaceutical composition comprising an effective amount of the compound of any one of Paragraphs A-F for treating pain in a subject, and a pharmaceutically acceptable carrier.

I. The pharmaceutical composition of Paragraph H, wherein the subject is suffering from acute and/or chronic pain.

J. A method comprising administering an effective amount of a compound of any one of Paragraphs A-F to a subject.

K. The method of Paragraph J, wherein the subject is suffering from acute and/or chronic pain.

L. A method comprising administering a pharmaceutical composition of Paragraph H or Paragraph I to a subject in need thereof.

M. The method of Paragraph L, wherein the subject is suffering from acute and/or chronic pain.

N. A method of binding the mu opioid receptor, the method comprising contacting a mu opioid receptor with a compound of any one of Paragraphs A-F.

O. The method of Paragraph N, wherein the contacting comprises a cell not within a patient.

Other embodiments are set forth in the following claims, along with the full scope of equivalents to which such claims are entitled.

What is claimed is:

1. A compound of Formula I:

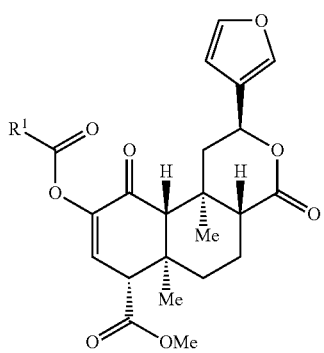

or a pharmaceutically acceptable salt and/or solvate thereof, wherein $R^1$ is

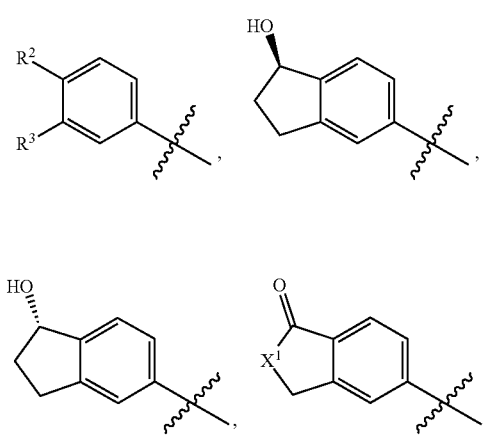

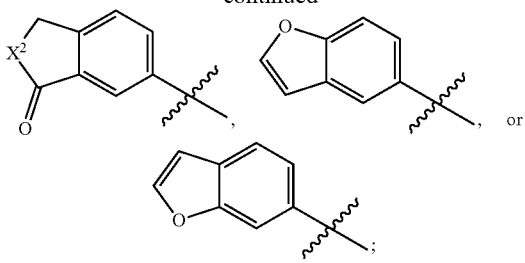

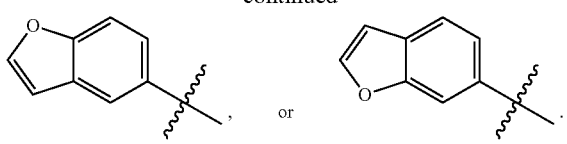

6. The compound of claim 1, wherein the compound is $R^2$ is hydroxyl-substituted $C_1$-$C_3$ alkyl, $C_1$-$C_3$ alkoxy substituted $C_1$-$C_3$ alkyl, —C(O)H, unsubstituted —C(O)—$C_1$-$C_3$ alkyl, or —C(O)—$NR^4R^5$;

$R^3$ is H, halo, hydroxyl-substituted $C_1$-$C_3$ alkyl, or $C_1$-$C_3$ alkoxy;

$R^4$ and $R^5$ are each independently H or unsubstituted $C_1$-$C_3$ alkyl; and $X^1$ and $X^2$ are each independently $CH_2$, O, or NH.

2. The compound of claim 1, wherein $R^1$ is

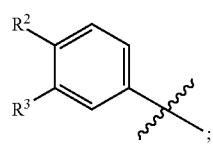

and $R^2$ is hydroxyl-substituted $C_1$-$C_3$ alkyl, $C_1$-$C_3$ alkoxy substituted $C_1$-$C_3$ alkyl, unsubstituted —C(O)—$C_1$-$C_3$ alkyl, or C(O)—$NH_2$.

3. The compound of claim 1, wherein $R^1$ is

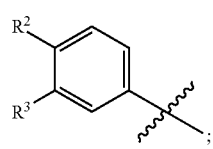

and $R^2$ is hydroxymethyl, (R)-1-hydroxyethyl, (S)-1-hydroxyethyl, methoxymethyl, or —C(O)—$NH_2$.

4. The compound of claim 1, wherein $R^3$ is H.

5. The compound of claim 1, wherein $R^1$ is

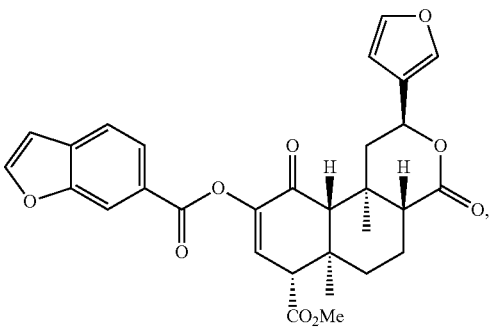

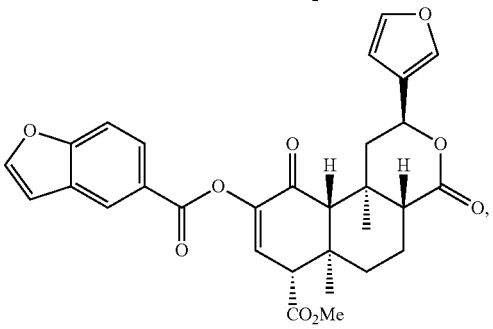

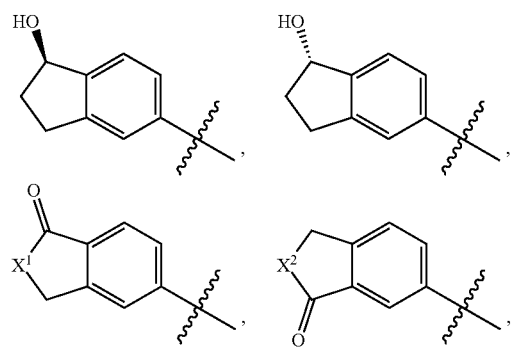

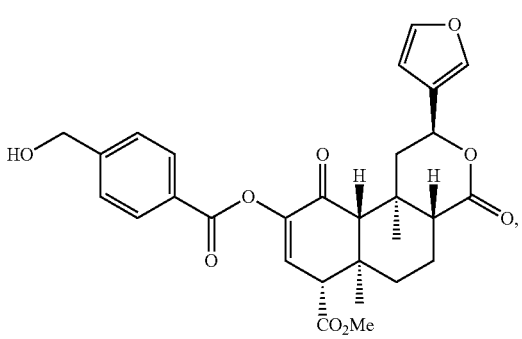

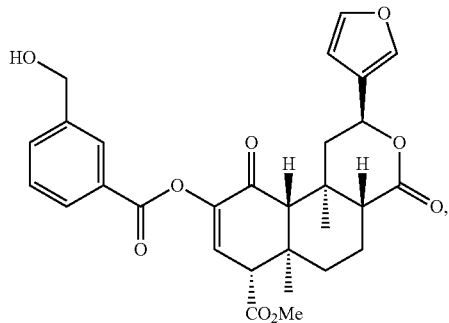

-continued

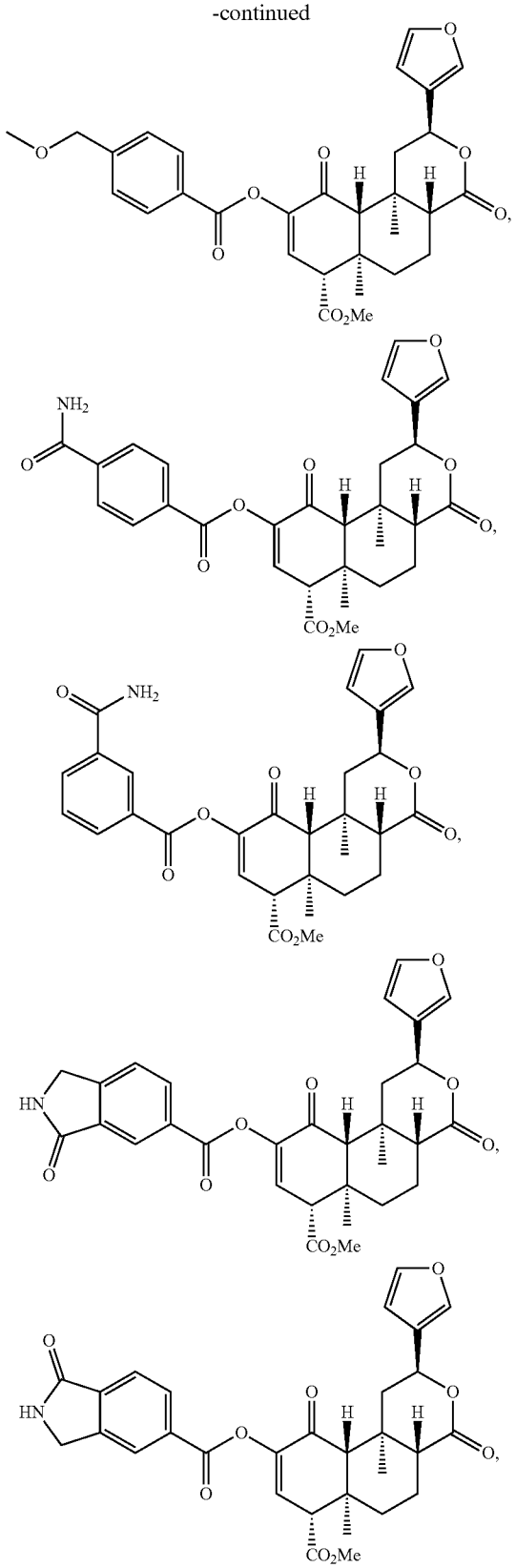

or a pharmaceutically acceptable salt and/or solvate thereof.

7. A composition comprising a compound of claim 1 and a pharmaceutically acceptable carrier.

8. A pharmaceutical composition comprising an effective amount of a compound of claim 1 for treating pain in a subject, and a pharmaceutically acceptable carrier.

9. A method comprising administering an effective amount of a compound of claim 1 for treating pain to a subject in need thereof.

10. The method of claim 9, wherein the subject is suffering from acute pain.

11. The method of claim 9, wherein the subject is suffering from chronic pain.

12. The method of claim 9, wherein $R^1$ is

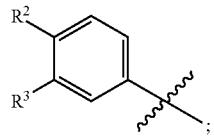

and $R^2$ is hydroxyl-substituted $C_1$-$C_3$ alkyl, $C_1$-$C_3$ alkoxy substituted $C_1$-$C_3$ alkyl, unsubstituted —C(O)—$C_1$-$C_3$ alkyl, or —C(O)—$NH_2$.

13. The method of claim 9, wherein $R^1$ is

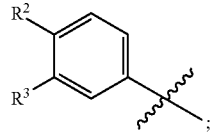

and $R^2$ is hydroxymethyl, (R)-1-hydroxyethyl, (S)-1-hydroxyethyl, methoxymethyl, or —C(O)—$NH_2$.

14. The method of claim 9, wherein $R^3$ is H.

15. The method of claim 9, wherein $R^1$ is

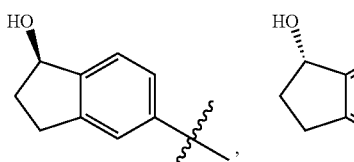

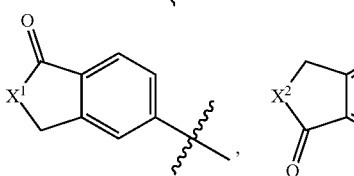

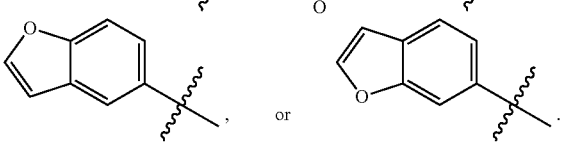

16. The method of claim 9, wherein the compound is
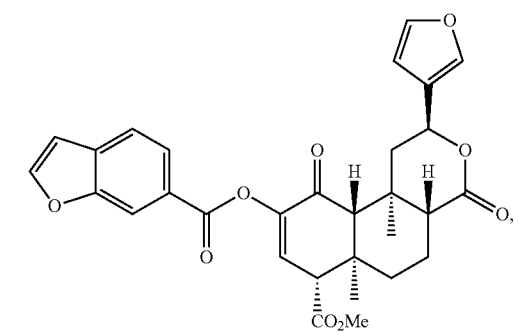
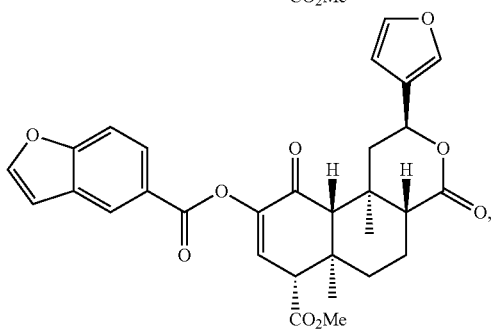
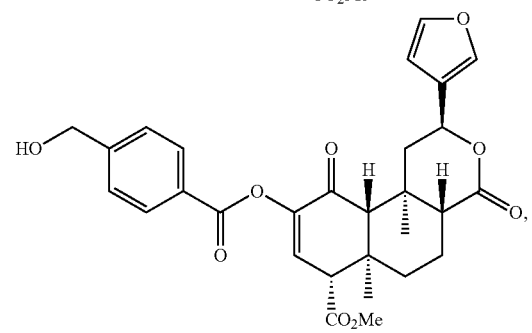
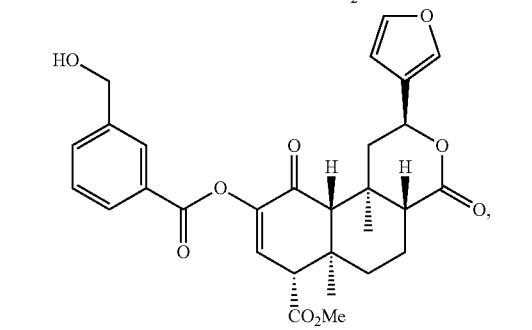
-continued
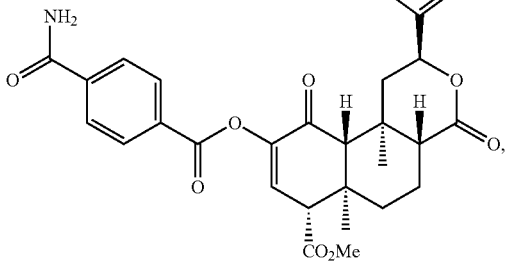
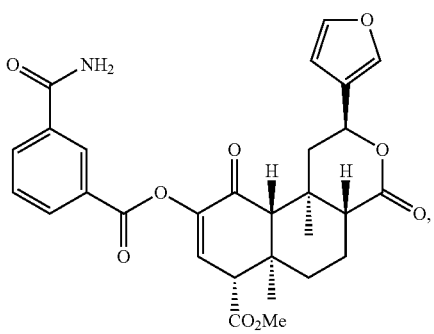
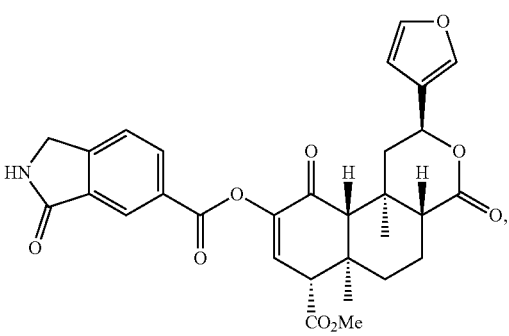
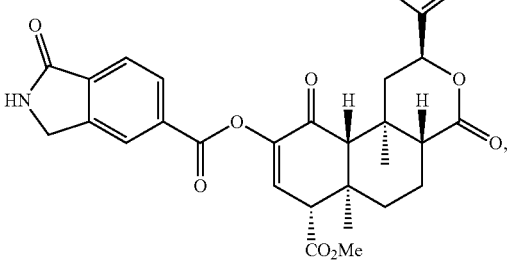
or a pharmaceutically acceptable salt and/or solvate thereof.
* * * * *